United States Patent
Lee

(10) Patent No.: US 8,074,784 B2
(45) Date of Patent: Dec. 13, 2011

(54) CONVENTIONAL TABLE FOR TESTING LIGHTS ALONG A CONVEYOR PATH

(75) Inventor: Robin Lee, Hamburg, NJ (US)

(73) Assignee: Production Resource Group, LLC, New Windsor, NY (US)

( * ) Notice: Subject to any disclaimer, the term of this patent is extended or adjusted under 35 U.S.C. 154(b) by 1037 days.

(21) Appl. No.: 11/952,742

(22) Filed: Dec. 7, 2007

(65) Prior Publication Data
US 2008/0134809 A1 Jun. 12, 2008

Related U.S. Application Data

(60) Provisional application No. 60/869,095, filed on Dec. 7, 2006.

(51) Int. Cl.
*B65G 47/00* (2006.01)
(52) U.S. Cl. .......... 198/617; 198/493; 324/407
(58) Field of Classification Search ........... 198/339.1, 198/340, 341.01, 341.07, 341.08, 493, 502.1, 198/502.2, 617; 702/81; 324/405, 407; 356/73
See application file for complete search history.

(56) References Cited

U.S. PATENT DOCUMENTS

| | | | | |
|---|---|---|---|---|
| 4,915,237 A * | 4/1990 | Chang et al. | ........... | 209/524 |
| 4,980,806 A * | 12/1990 | Taylor et al. | ........... | 362/85 |
| 5,273,392 A * | 12/1993 | Bernard et al. | ........... | 414/807 |
| 5,659,491 A * | 8/1997 | Ichikawa et al. | ........... | 702/65 |
| 6,116,404 A * | 9/2000 | Heuft et al. | ........... | 198/339.1 |
| 6,244,075 B1 * | 6/2001 | Patel et al. | ........... | 65/483 |
| 6,519,837 B1 * | 2/2003 | Ichikawa et al. | ........... | 29/720 |
| 6,520,311 B1 * | 2/2003 | Maeda et al. | ........... | 198/339.1 |
| 6,769,536 B2 * | 8/2004 | Lutz | ........... | 198/861.1 |
| 7,505,064 B2 * | 3/2009 | Knoedgen et al. | ........... | 348/187 |
| 7,654,379 B2 * | 2/2010 | Boberg et al. | ........... | 198/341.08 |
| 7,673,736 B2 * | 3/2010 | Kowalchuk | ........... | 198/478.1 |

* cited by examiner

*Primary Examiner* — Douglas Hess
(74) *Attorney, Agent, or Firm* — Law Office of Scott C. Harris, Inc.

(57) ABSTRACT

A testing table that allows testing lights along its length. The testing table can be used to convey lights along the direction, and to test the lights at different locations along the direction along the conveying. The lights can be cleaned and tested. Empty tubs can be returned.

5 Claims, 3 Drawing Sheets

CONVENTIONAL TABLE FOR TESTING LIGHTS ALONG A CONVEYOR PATH

The present application claims priority from provisional application No. 60/869,095, filed Dec. 7, 2006, the disclosure of which is herein incorporated by reference.

BACKGROUND

Stage lights are often used for mobile setups in which the state lights are rented for an event and then returned. Once returned, the stage lights should be tested in order to get them ready for the next rental cycle.

The stage lights can be heavy, and can include multiple different parts, all of which need to be inventoried and made ready for their next rental.

SUMMARY

The present application discloses a special technique used for cleaning sorting and checking lights which has special features and functions adapted for operating in this way.

BRIEF DESCRIPTION OF THE DRAWINGS

These and other aspects will now be described with reference to the accompanying drawings, wherein.

DETAILED DESCRIPTION

Figure 1:
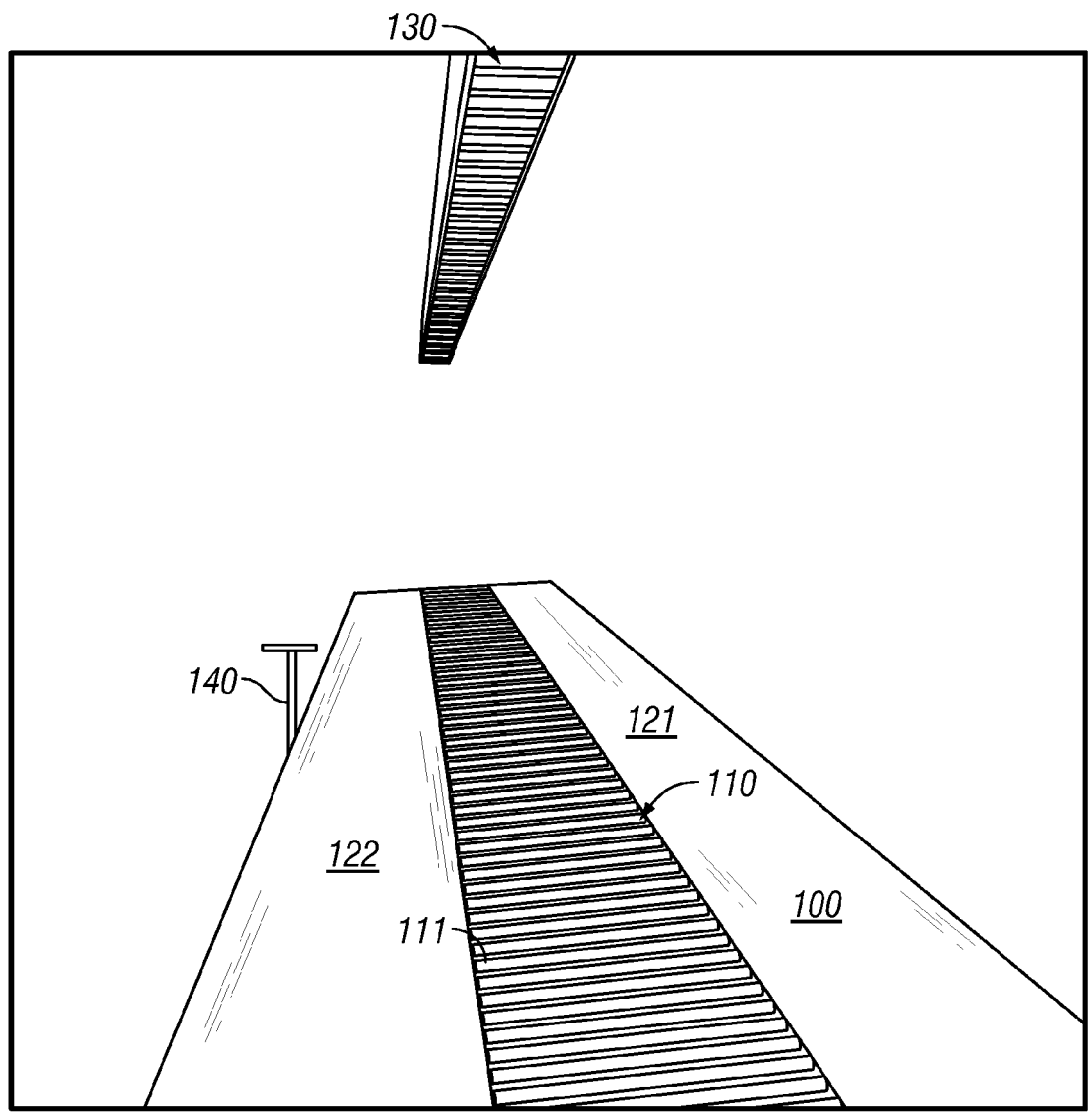
FIG. 1 shows a perspective view of the conventional table including its different parts.

FIG. 1 illustrates an overall embodiment showing a table. The table includes a conveying part, and a number of support equipment adjacent to the conveying part. The support equipment is respectively used for different parts of handling the light.

In an embodiment, a central portion defines a moving area 110 with a number of open slats that forms an endless loop for conveying lights and light parts. The two sides of that moving portion respectively define work areas. For example, a first side 122 defines a first work area and a second side 121 defines a second work area.

Any of the non-moving areas along the table define sections that may include a worker, or automatic robot, or other similar structure that can be used for processing the lights. Any of these structures can remove a containerized or non-containerized part, e.g., in a crate or bin, off of the movable area onto one of the non-movable areas 121 122. This enables workers to work on both sides of the table. Any worker can pull any item off of the conveyor and put it on the non-movable area. Two different workers can work simultaneously on two different sides at the same time.

An overhead tool holding part 130, such as a truss, may also be used to hold testing tools and equipment. The truss may be directly over the moving area 110, or there may be two different trusses respectively over either of the non-movable areas.

Lights to be tested can be located on the moving area 110, and the non-moving area 121,122, and moved from one area to the other. For example, there may be different stations for carrying out different operations. A first of the stations 140 may have a number of parts for carrying out first maintenance operation on the lights. The different parts are described herein for example. The stations may include a lens washer station, with air reels and/or power reels, reels that extend from the sides or from above, paint and air blast stations, and blowoff stations. These different stations may be located at different locations. There may also be sandblast and bead blast boots for more difficult cleaning. These different stations at least some areas are described herein.

In an embodiment, one issue with the lights is that after rental, the lights are very often returned in extremely dirty condition. The lights need cleaning in order to put them in a form where they can be re-rented.

In the embodiment, the conveyor includes openings therein, which may be formed between slats, or may be formed of a belt formed of various parts with different openings. The openings allow the dirt etc to be removed from the lights and pass downward between the slats. In one embodiment, for example, air draft portions may continually be blowing on the lights to blow the debris off the lights.

Figure 2:
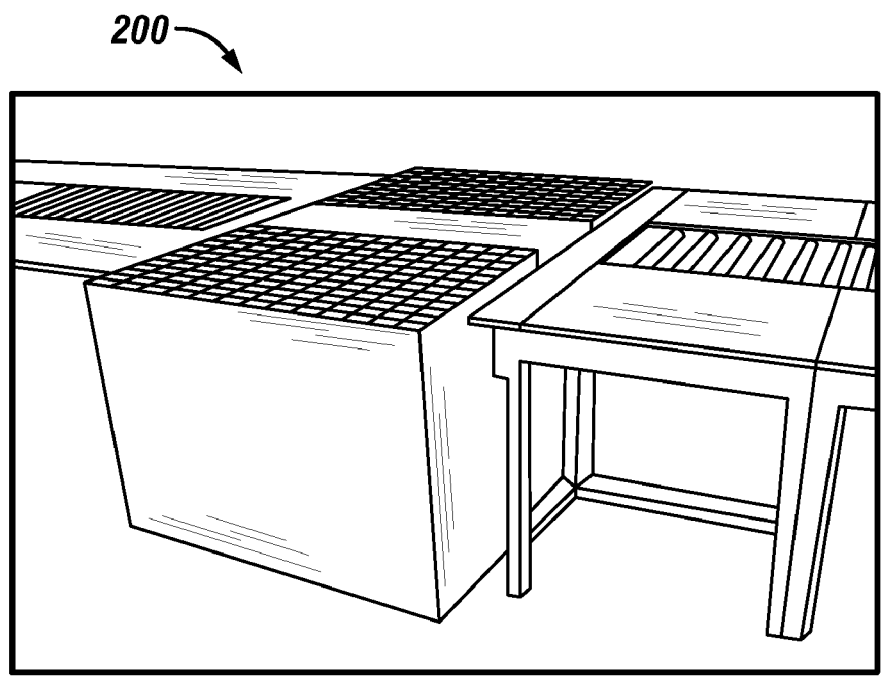
FIG. 2 shows a downdraft portion of the tables.

FIG. 2 illustrates a first area which is a downdraft stage. In this area, very intense and fast-moving air is sucked down across the lights. The downdraft creates a suction of air with a downward pull. This may remove loose dust and dirt. The downdraft section may blow from above, e.g. from a device attached to the overhead truss 130, and also may suck from below, e.g. using a suction unit 210. High velocity air, e.g. moving between 50 and 100 mph may be used to pull the dirt off of the light in this way.

Figure 3:
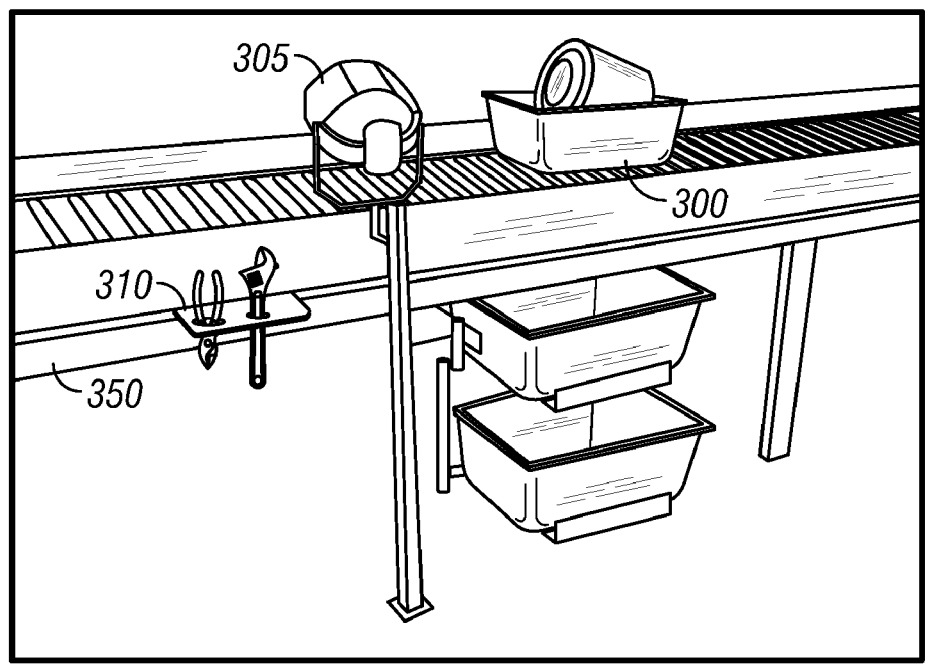
FIG. 3 shows a different side view of portions of the table and the crate return.

FIG. 3 illustrates another section. The lights can be located in tubs such as tub 300. The lights may be assembled or disassembled when in the tubs. Any of the tubs can be pulled off to one of the sides. A mount for the lights is shown as 305, and a vice for the lights is shown as 310. The lights may be attached at mount 305, for example, and powered for various purposes associated with testing. The lights can be powered at the stations using a power connector at the station, and, once powered, light can be projected light on to a screen adjacent the conveyor which allows displaying light to test a focus of the light. The stations can also have a control connector for the light, which control connector operates to cause the light to project a specified projection.

Many other stations as described herein may also be located along the device.

Once the tubs such as 300 reach their far end, they can be returned as described further herein. The embodiment may use, for example, an endless loop conveyor that allows the empty tubs to be returned to the beginning.

Figure 4:
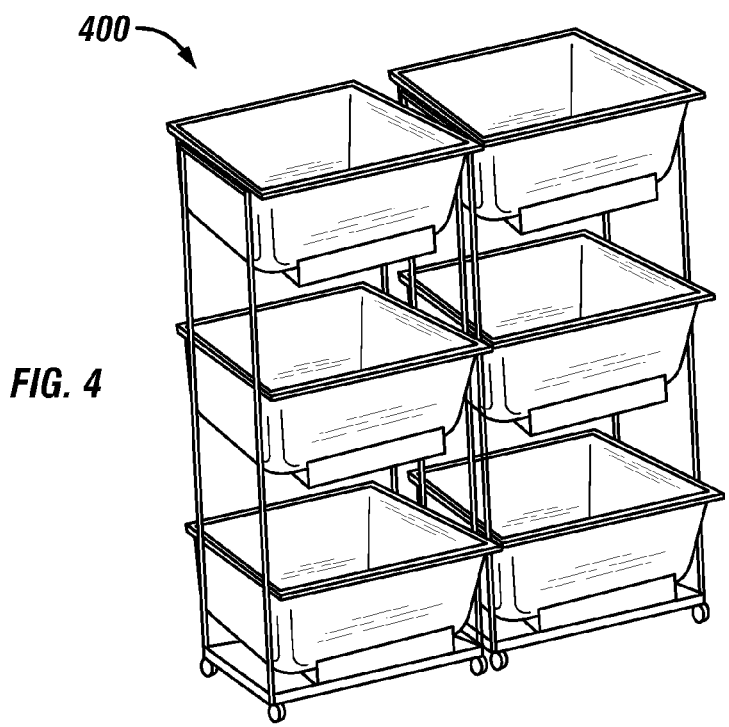
FIG. 4 shows crate storage.

While the top portion includes the two nonmovable portions shown respectively as 121 and 122, the bottom portion does not include those and hence can be much thinner. The bottom layer of the table is shown in FIG. 3, with the empties 350 being returned along that bottom layer. Those empties, for example, may be on the much thinner bottom layer that can be returned. Since the bottom portion is much thinner, it includes the ability to provide additional storage areas adjacent the bottom portion. For example, FIG. 4 illustrates plural different parts racks being underneath the device. The parts racks 400 may include parts that can be used at each of the stations. For example, the part rack 400 may be used adjacent the station that is used for holding parts that are associated with the testing and carried out near that station.

Figure 5:
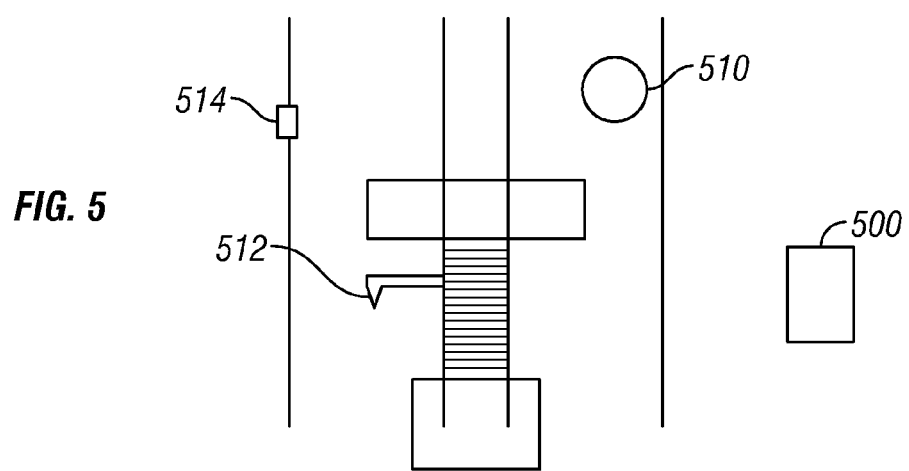
FIG. 5 shows the way that the different items can be handled.

FIG. 5 illustrates a top view of the downdraft area, and shows a number of different things that may exist in that area. The downdraft table may also have air reels and power reels such as 510 located close to the draft downdraft area. Tools such as 512 may also be used. For example, tools may be attached to cables to allow the tools to be moved, but which prevent those tools from being removed from the station. Those tools are associated with control and/or other kinds of repair of the lights.

The air reels may be used to blow off any specifically difficult dirt. In addition, one of the mounts such as 514 may be associated with a screen 500. That screen 500 can be allowed to test the light for focusing.

Figure 6:
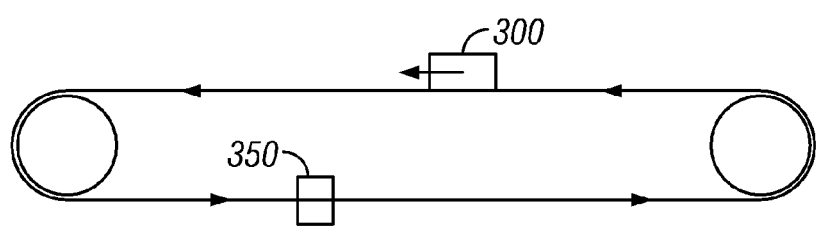
FIG. 6 shows the endless loop conveyor.

FIG. 6 illustrates the conveyor from above, and illustrates how once the tubs such as 300 reach the end, they can be removed from the conveyor and placed on the return part of the conveyor 350.

What is claimed is:

1. A method of testing lights, comprising:
   conveying lights along a conveyor, to a plurality of different stations;
   at one of said stations, cleaning dirt off of the light;
   at another of said stations, powering the light, using a power connector at said another station, and projecting light on to a screen adjacent the conveyor which allows displaying light to test a focus of the light.

2. A method as in claim 1, wherein said another station includes a mount for the light, and a power connector for the light as well as a control connector for the light, which control connector operates to cause the light to project a specified projection.

3. A method as in claim 1, wherein said conveying comprises conveying lights in a first direction, and conveying empty light holding tubs in a second direction opposite to said first direction.

4. A method as in claim 3, wherein a width of the overall device in said first direction is wider than a width of the overall device in said second direction.

5. A method as in claim 1, wherein said cleaning dirt comprises cleaning the dirt at a downdraft station.

* * * * *